(12) United States Patent
Beavers

(10) Patent No.: US 12,226,330 B2
(45) Date of Patent: Feb. 18, 2025

(54) SYSTEMS, METHODS, AND TECHNIQUES FOR EYE GAZE CONTROL OF SEAT AND BED POSITIONING

(71) Applicant: Jay Curtis Beavers, Duvall, WA (US)

(72) Inventor: Jay Curtis Beavers, Duvall, WA (US)

( * ) Notice: Subject to any disclaimer, the term of this patent is extended or adjusted under 35 U.S.C. 154(b) by 417 days.

(21) Appl. No.: 17/495,776

(22) Filed: Oct. 6, 2021

(65) Prior Publication Data

US 2022/0104959 A1   Apr. 7, 2022

Related U.S. Application Data

(60) Provisional application No. 63/088,451, filed on Oct. 7, 2020.

(51) Int. Cl.
*A61F 4/00* (2006.01)
*A61G 5/00* (2006.01)
(Continued)

(52) U.S. Cl.
CPC .................. *A61F 4/00* (2013.01); *A61G 5/00* (2013.01); *A61G 7/018* (2013.01); *G05B 19/042* (2013.01);
(Continued)

(58) Field of Classification Search
CPC ... A61F 4/00; A61G 2203/18; A61G 2203/20; A61G 5/00; A61G 5/1056; A61G 7/018;
(Continued)

(56) References Cited

U.S. PATENT DOCUMENTS

| 4,323,829 A | 4/1982 | Witney et al. |
| 4,767,940 A | 8/1988 | Tuttle |

(Continued)

FOREIGN PATENT DOCUMENTS

| CN | 105892691 A | 8/2016 |
| CN | 106074021 B | 2/2018 |

(Continued)

OTHER PUBLICATIONS

International Search Report and Written Opinion issued in PCT Application No. PCT/US2021/054053, international filing date Oct. 7, 2021, issued Jan. 13, 2022.

(Continued)

*Primary Examiner* — Tameem D Siddiquee
(74) *Attorney, Agent, or Firm* — Lowe Graham Jones PLLC; Ellen M. Bierman

(57) ABSTRACT

Methods, systems, and techniques for controlling posture by using eye gaze technology to facilitate position changes in seating, such as in a wheelchair or bed, are provided. Example embodiments provide an Eye Gaze Posture Control System ("EGPCS") which enables people with advanced motor neuron diseases or disabilities like amyotrophic lateral sclerosis or muscular dystrophy to use eye gaze technologies to control their seating and bed positioning. In one embodiment, the example EGPCS comprises a posture and pressure advisor, logging and telemetry logic, a posture control application, device interface(s) to one or more other devices that control aspects of the powered wheelchair or bed, and eye gaze actuation control. These components cooperate to adjust position of a seat or a bed using eye gaze technology as opposed to by a virtual cursor or by manual control.

24 Claims, 14 Drawing Sheets

(51) Int. Cl.
*A61G 7/018* (2006.01)
*G05B 19/042* (2006.01)
*G06F 3/01* (2006.01)

(52) U.S. Cl.
CPC .......... *G06F 3/013* (2013.01); *A61G 2203/18* (2013.01); *A61G 2203/20* (2013.01); *G05B 2219/2608* (2013.01); *G05B 2219/2637* (2013.01)

(58) Field of Classification Search
CPC .......... G06F 3/011; G06F 3/012; G06F 3/013; G06F 3/015; G05B 19/042; G05B 2219/2608; G05B 2219/2637
See application file for complete search history.

(56) References Cited

U.S. PATENT DOCUMENTS

| | | | |
|---|---|---|---|
| 6,424,338 | B1 | 7/2002 | Anderson |
| 8,862,307 | B2 | 10/2014 | Pettersson et al. |
| 2008/0097256 | A1* | 4/2008 | Torres .................... A61G 5/045 601/24 |
| 2008/0132383 | A1 | 6/2008 | Einav et al. |
| 2010/0212087 | A1* | 8/2010 | Leib ....................... A61G 12/00 5/81.1 R |
| 2012/0046821 | A1 | 2/2012 | Pettersson et al. |
| 2016/0101664 | A1 | 4/2016 | Richter |
| 2016/0267708 | A1* | 9/2016 | Nistico ................ H04N 13/344 |
| 2018/0014988 | A1 | 1/2018 | Diaz-Flores et al. |
| 2018/0135987 | A1* | 5/2018 | Evans .................... G01C 21/20 |
| 2020/0022577 | A1* | 1/2020 | Rishoni ................. G06F 3/0482 |
| 2020/0324152 | A1 | 10/2020 | Goldfish et al. |
| 2021/0240259 | A1* | 8/2021 | Bull ........................ G06F 3/013 |

FOREIGN PATENT DOCUMENTS

| | | |
|---|---|---|
| CN | 109662842 A | 4/2019 |
| JP | 2018-529171 | 10/2018 |
| KR | 10-0488684 | 5/2005 |
| WO | 01/26599 | 4/2001 |
| WO | 2007/120099 A1 | 10/2007 |
| WO | 2018/090109 A1 | 5/2018 |

OTHER PUBLICATIONS

Barea, et al., "EOG Technique to Guide a Wheelchair," 7 pages.
Barea, et al., "System for Assisted Mobility Using Eye Movements Based on Electrooculography," IEEE Transactions on Neural Systems and Rehabilitation Engineering, vol. 10, No. 4, Dec. 2002, pp. 209-218.
Bartolein, C., et al., "Multilevel Intention Estimation for Wheelchair Control," Proceedings of the European Control Conference 2007, Jul. 2-5, 2007, pp. 5463-5470.
Bates, R., et al., "Introducing Cogain—Communication by Gaze Interaction," 8 pages.
Bien, Z., et al., "Development of a Wheelchair-based Rehabilitation Robotic System (KARES II) with Various Human-Robot Interaction Interfaces for the Disabled," Proceedings of the 2003 IEEE/ASME, International Conference on Advanced Intelligent Mechatronics (AIM 2003), pp. 902-907.
Fehr, L., et al., "Adequacy of Power Wheelchair Control Interfaces for Persons with Severe Disabilities: A Clinical Survey," Journal of Rehabilitation Research and Development, Department of Veterans Affairs, vol. 37, No. 3, May/Jun. 2000, pp. 353-360.
Felzer, T., et al., "HaWCoS: The 'Hands-Free' Wheelchair Control System," pp. 127-134.
Kar, A., "A Review and Analysis of Eye-Gaze Estimation Systems, Algorithms and Performance Evaluation Methods in Consumer Platforms," Accepted for Publication in IEEE Access. DOI 10.1109/Access 2017, 25 pages.
Law, C., et al., "A Cap as Interface for Wheelchair Control," Proceedings of the 2002 IEEE/RSJ International Conference on Intelligent Robots and Systems EPFL, Lausanne, Switzerland, Oct. 2002, pp. 1439-1444.
Lee, D., et al., "Biological Surface Electromyographic Switch and Necklace-Type Button Switch Control as an Augmentative and Alternative Communication Input Device: a Feasibility Study," Australasian Physical & Engineering Science in Medicine, vol. 42, 2019, pp. 839-851.
Lin, C., et al., "Powered Wheelchair Controlled by Eye-Tracking System," Optical Applicata, vol. 36, No. 2-3, 2006, pp. 401-412.
Mazo, M., et al., "An Integral System for Assisted Mobility," IEEE Robotics & Automation Magazine, Mar. 2001, pp. 46-56.
Miller, D., et al., "A Robotic Wheelchair," American Institute of Aeronautics and Astronautics, Inc., 1993, pp. 407-411.
Nicolas-Alonso, L., et al., "Brain Computer Interfaces, a Review," Sensors, 2012, vol. 12, pp. 1211-1279.
Wastlund, E., et al., "What You See is Where You Go: Testing a Gaze-Driven Power Wheel-chair for Individuals with Severe Multiple Disabilities," ETRA 2010, Austin, Texas, Mar. 22-24, 2010, pp. 133-136.
Wastlund, E., et al., "Evaluating Gaze-Driven Power Wheelchair with Navigation Support for Persons with Disabilities," Jul. 9, 2021, 17 pages.

* cited by examiner

SYSTEMS, METHODS, AND TECHNIQUES FOR EYE GAZE CONTROL OF SEAT AND BED POSITIONING

CROSS-REFERENCE TO RELATED APPLICATION

This application claims the benefit of priority from U.S. Provisional Patent Application No. 63/088,451, entitled "Systems and Methods for Controlling Seat Positioning with Eye Gaze," filed Oct. 7, 2020, which application is incorporated herein by reference in its entirety.

TECHNICAL FIELD

The present disclosure relates to methods, techniques, and systems for control of seat and bed positioning and, in particular, to methods, techniques, and systems for seat and bed positioning using eye gaze control.

BACKGROUND

Powered chairs and beds are commonly used to provide comfort and pressure relief for people who are mobility disabled, permanently or temporarily. There are many situations where these devices are motorized to enable position control and pressure relief, such as hospital beds, powered recliner chairs, and complex rehabilitation powered wheelchairs. These devices are generally controlled using hands.

Currently, these powered positioning systems use a simple button control system movable using fingers, typically with up three or four axes of control and two directions of movement on each axis. In some situations, people with certain disabilities, such as people with advanced motor neuron diseases or disabilities like amyotrophic lateral sclerosis, muscular dystrophy, or spinal cord injury, cannot use their own hands to control button-based control systems, leaving them at the mercy of their caregivers to understand their physical needs and make positioning changes on their behalf.

DETAILED DESCRIPTION

Figure 1:
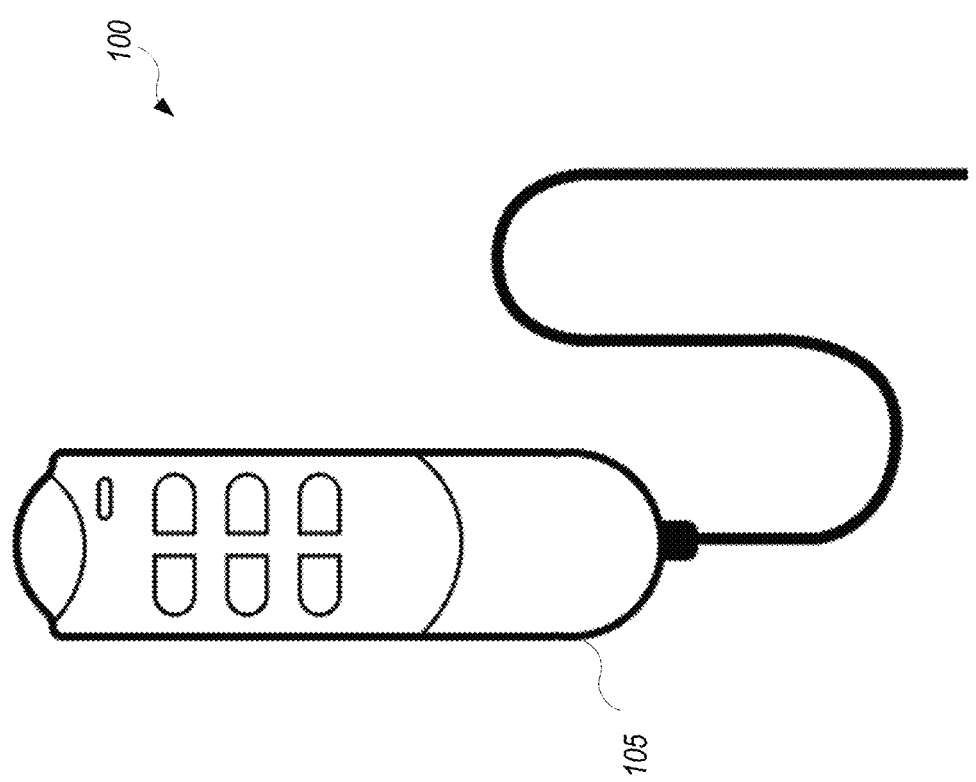
FIG. 1 is a block diagram of a current three axis remote control actuated via fingers.

Embodiment described herein provide enhanced systems, methods, and techniques for a person to control their body's posture by using their eyes to gaze on virtual buttons on a display to facilitate position changes in seating, such as in a wheelchair or bed. Example embodiments provide an Eye Gaze Posture Control System ("EGPCS") which enables people with advanced motor neuron diseases or disabilities like amyotrophic lateral sclerosis or muscular dystrophy to use eye gaze technologies previously primarily used to generate speech to control their seating and bed positioning. The improved techniques of an EGPCS seek to restore independence to people with disabilities that do not otherwise enable them to reliably use traditional button-based or joystick like control system by a more efficient and natural mechanism that is more immediately responsive.

In one example EGPCS, a powered wheelchair is equipped with a tablet computer mounted in front of the wheelchair occupant and connected to the control system of the powered wheelchair. The tablet computer has a camera on it which views the person's eyes (an "eye gaze camera") and then uses well known algorithms (executing on a microcontroller) to determine where the person is looking on the screen. In some cases, the eye gaze camera is a discrete device and in other cases the eye gaze camera is integrated into the chassis of the display. The eye gaze camera sensor can be as simple as an RGB digital camera or it can be a combination of one or more specialty components designed to enhance the precision and computation of eye gaze location, such as by using IR filtered cameras, IR light emitters, and dedicated coprocessors. Examples of eye gaze algorithms for use with such devices include those described in "https://www.tobiipro.com/learn-and-support/learn/eye-tracking-essentials/how-do-tobii-eye-trackers-work/" and in "https://en.wikipedia.org/wiki/Eye_tracking, Technologies and techniques," which are incorporated herein by reference in their entireties. In an example EGPCS, the tablet is executing an application which presents user interface controls such as virtual buttons which actuate (e.g., are selected/clicked) when the person looks at the button continuously for a period of time. As the person continues to look at the button, it becomes 'pressed' to allow the person to select the duration of control and therefore the amount of position change.

A similar EGPCS may be used to control a powered positioning bed, such as a hospital bed or powered reclining chair. Typically, a hospital bed is equipped with a tablet computer mounted on a nearby wall or ceiling and connected to a control system of the hospital bed positioning system. Similar to the tablet computer used with a powered wheelchair, the tablet computer used with a powered positioning bed has an associated camera which views the person's eyes and an application which presents virtual buttons which are eye gaze actuated.

In addition, various alternatives and enhancements may be incorporated in an example EGPCS including use of a head mounted display or using a room display and camera. For example, a head mounted display such as augmented reality glasses may be used to display control buttons and detect eye gaze position. Example AR glasses for use with EGPCS embodiments include, for example, Microsoft Holo-Lens ("https://docs.microsoft.com/en-us/windows/mixed-reality/design/eye-tracking") or Tobii Pro Glasses 3 ("https://www.tobiipro.com/product-listing/tobii-pro-glasses-3/"). In such scenarios, the display and cameras are attached to the glasses. Algorithms and microcontrollers may or may not be contained in the glasses themselves. For example, Microsoft HoloLens collate the display, cameras, and processing all on the head mounted device. As another example, Tobii Pro Glasses provide an implementation where just the eye gaze cameras are located on the head mounted device, and the display and computation are separately mounted. As well, a room display and camera, such as a wall or ceiling mounted display or surface, may be used to present actuation buttons and detect eye gaze position. For example, the television screen in a hospital room can be eye gaze enabled to allow control of the hospital bed position. In another example, an ICU (intensive care unit) room may include an eye gaze enabled display mounted above the bed to allow for posture control. In another example, user interface controls may be projected on a wall or ceiling and an eye gaze camera used to detect and recognize eye gaze position and cause activation of the wheelchair/bed/chair actuators.

FIG. 1 is a block diagram of a current three axis remote control actuated via fingers. The remote control 105 has three pair of buttons, each button increases or decreases the position of one axis of movement allowing a person to change his/her posture one step at time. Holding down a button typically results in a continuous change in position in the direction indicated. Powered seating wheelchairs, hospital beds, and powered reclining chairs come with some variation of this type of controller. Controller 105 is a three-axis controller that supports changing posture such as recline, leg lift, and tilt.

Figure 2:
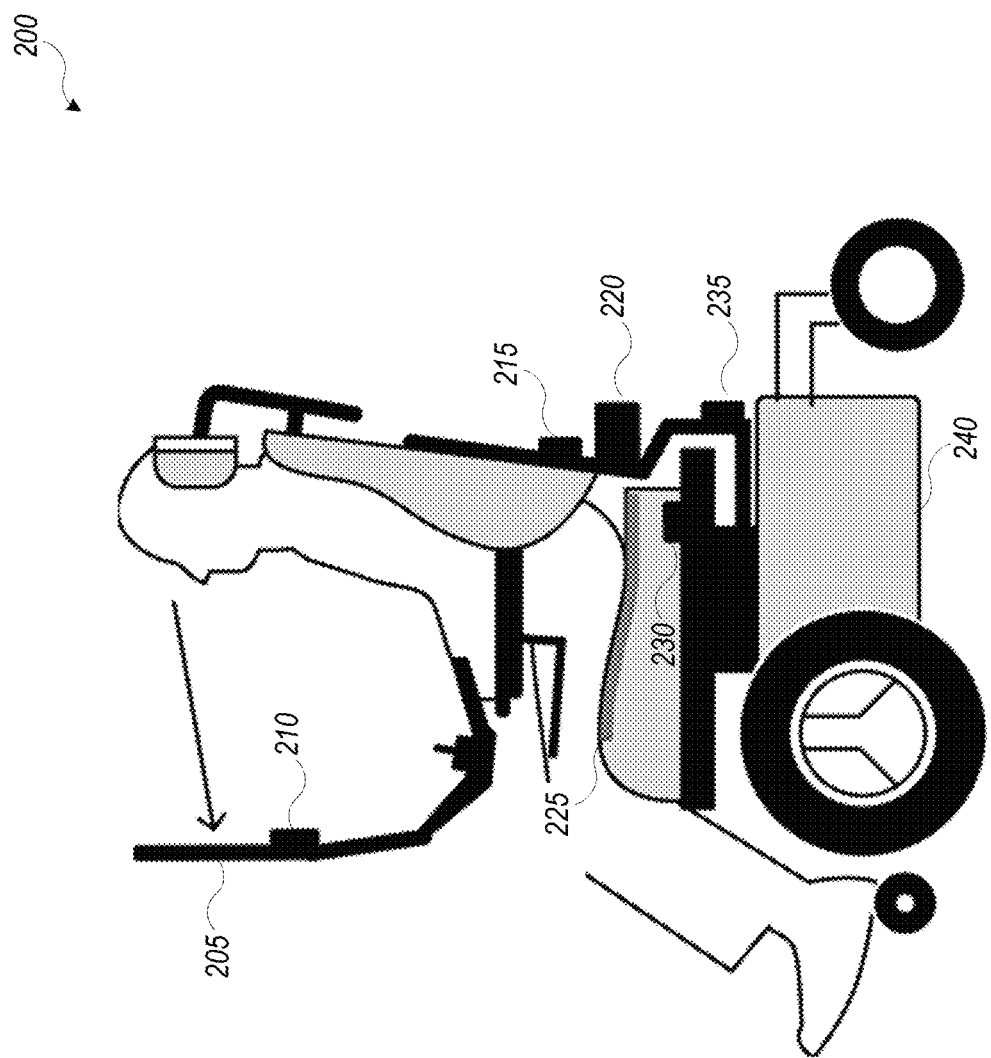
FIG. 2 is an example block diagram of an example powered wheelchair with powered adjustable seating according to an example Eye Gaze Posture Control System.

FIG. 2 is an example block diagram of an example powered wheelchair with powered adjustable seating according to an example Eye Gaze Posture Control System. The EGPCS has a display 205 which shows a user interface which provides visual targets (e.g., user interface controls or buttons) which can be actuated (e.g., clicked or selected) through detection of a gaze using X/Y coordinates on the display through eye gaze sensors 210. User intent to change positioning is then translated into commands sent to one or more posture controllers 215 which translate the commands coming from the display device into seating actuator controller 220 commands. The seating actuator controller 220 then provides power and direction to the seating axis actuators (not shown) embedded in the powered chair chassis which result in a change in posture. Pressure observing sensors and fabrics 225 detect and calculate the amount of pressure the current posture is applying to the skin of the end user, and this is communicated to the display 205 through the pressure monitor 230 (a smart sensor) which analyzes the raw input from the sensors and fabrics 225, turns this into a data set of pressure points, and communicates the dataset to the EGPCS. Additional inputs, actuators, and sensors can be attached to the EGPCS, some examples of which are wheelchair driving controllers, push button switches, cameras, and camera point/tilt/pan systems, and the like.

Figure 3:
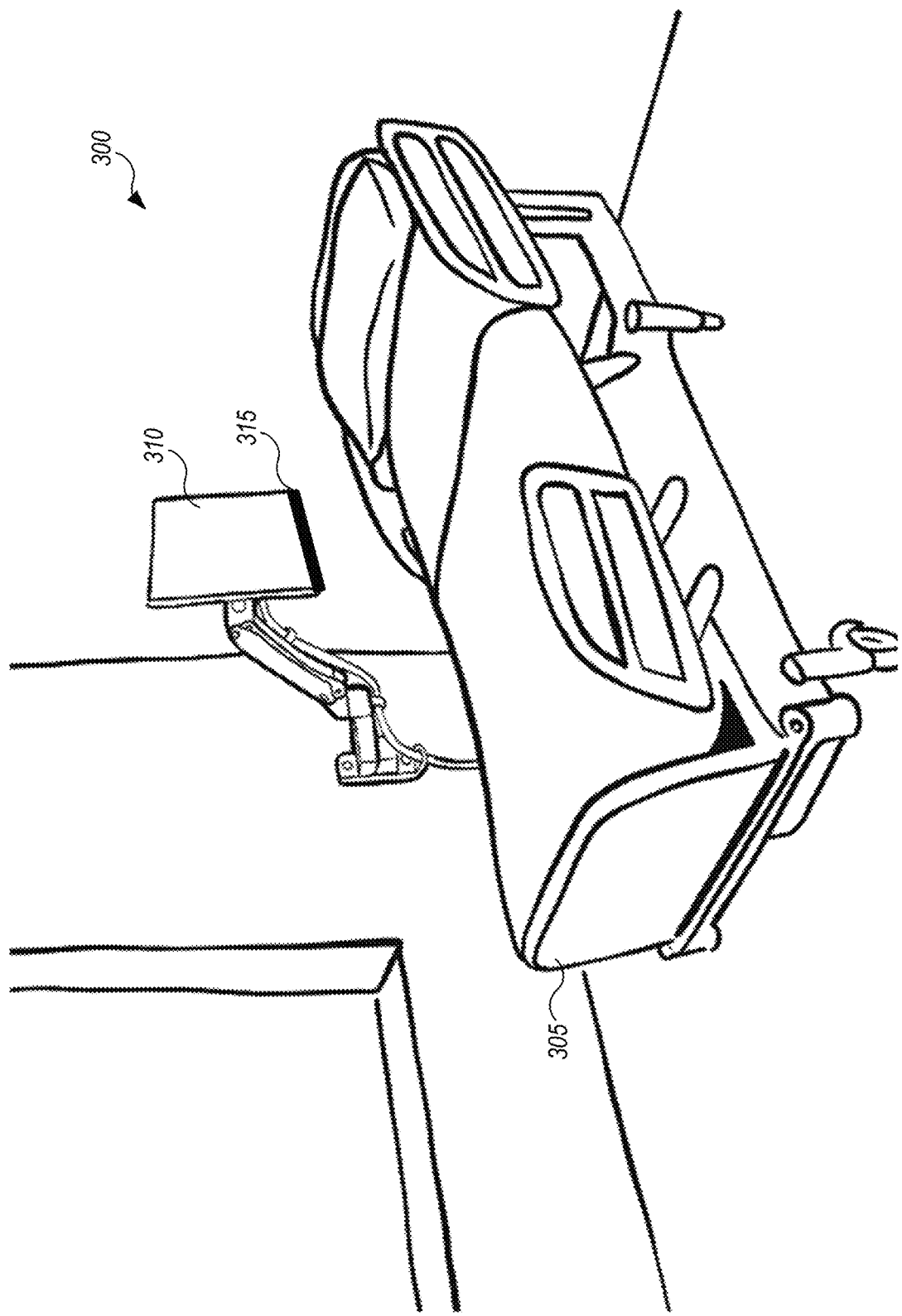
FIG. 3 is an example block diagram of an example powered hospital bed with powered adjustable positioning according to an example Eye Gaze Posture Control System.

FIG. 3 is an example block diagram of an example powered hospital bed with powered adjustable positioning according to an example Eye Gaze Posture Control System. These components include but are not limited to the powered repositionable bed 305, display 310, and eye gaze sensor 315. In some examples, the display 310 and eye gaze sensors 315 could be mounted to the bed frame, a wall, ceiling, or floor mount. In other examples, the display 310 and eye gaze sensors 315 can be head-mounted through systems referred to as 'augmented reality glasses' or 'virtual reality goggles.' Other configurations are possible.

Figure 4:
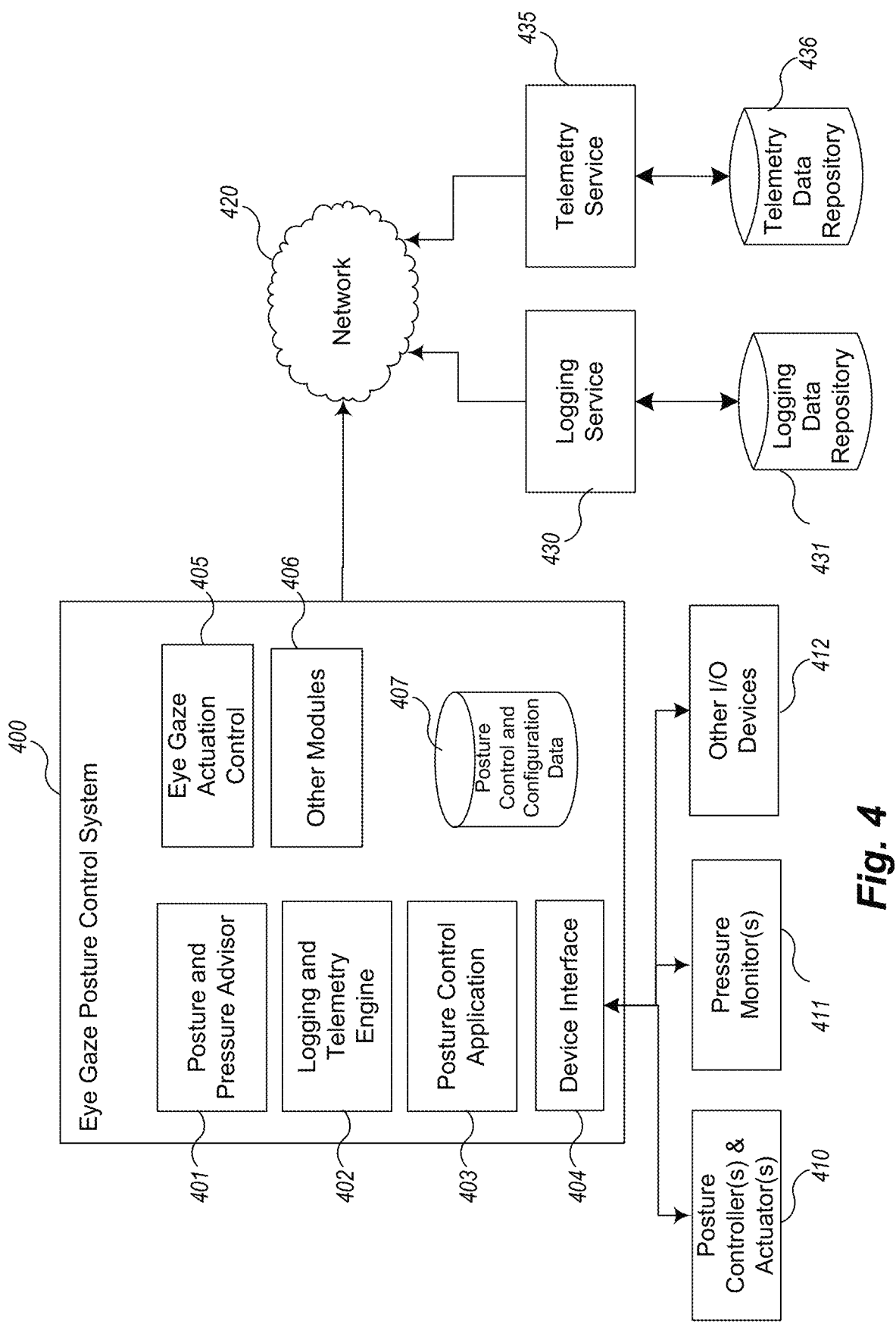
FIG. 4 is an example block diagram of components of an example Eye Gaze Posture Control System.

FIG. 4 is an example block diagram of components of an example Eye Gaze Posture Control System. In one example embodiment, the EGPCS comprises one or more functional components/modules that work together to adjusting position of a seat or a bed (or equivalent) using eye gaze technology as opposed to by a virtual cursor or by manual (hand) control. For example, an example Eye Gaze Posture Control System may comprise a posture and pressure advisor logic 401, logging and telemetry engine/logic 402, a posture control application that interacts with the disabled user, a device interface(s) to one or more other devices that control aspects of the powered wheelchair or bed, eye gaze actuation control 405, other modules 406, and posture control and configuration data 407. The posture and pressure advisor 401 is logic that runs in the background measuring the pressure and duration of pressure of the end user on the seat/bed in order to advise or prevent against positioning that may endanger the end user. For example, in a paper entitled, "Assessing evidence supporting redistribution of pressure for pressure ulcer prevention," Journal of Rehabilitation Research & Development Vol. 48 No. 3, pressures of 500 mmHG for four hours induced ulcers in swine tissue but pressures of 150 mmHG did not induce ulcers. Accordingly, an example posture control advisor would recommend position changes hourly when pressures hotspots in excess of 150 mmHH were detected by, for example, pressure monitor 230.

The eye gaze actual control 405 is code logic for reading a stream of eye status and X/Y coordinates from the eye gaze camera (e.g., eye gaze sensors 210 and 315). These coordinates are calculated using algorithms described elsewhere, as they are developed by third parties who typically make eye gaze camera devices. For example, in dark pupil eye tracking algorithms, polynomial transformations are used to calculate the vectors for gaze direction and head orientation and these vectors are then used to project the intersection point of the eye gaze onto the 2D plane of the display surface. See, for example, Kar, A. and Corcoran, P., "A Review and Analysis of Eye-Gaze Estimation Systems, Algorithms and Performance Evaluation Methods in Consumer Platforms," accepted for publication in IEEE ACCESS. DOI 10.1109/ACCESS.2017.2735633, available at "https://arxiv.org/ftp/arxiv/papers/1708/1708.01817.pdf" which is incorporated herein by reference in its entirety. The stream of X/Y coordinates are then used to determine when an 'eye fixation' occurs on an on-screen button (or other user interface actuation area). Typically, an eye fixation is determined when the X/Y coordinate data stream has stayed inside the bounding box (e.g., area of the on-screen button)

for a fixed period of time, with random noise data variations 'smoothed' out of the data stream using a noise reduction technique such as a Kalman filter. The button is considered 'pressed' or activated when the X/Y data stream is within the bounding box and 'released' or deactivated when the X/Y data stream leaves the bounding box. The loss of the stream of valid coordinates, either through closing of the eyes or looking away from the display surface, causes an immediate deactivation of all control elements.

The logging and telemetry logic 402 interacts with a (in some embodiments external) logging services 430 to collect and log data, such as age, preferences, events, device interactions, warnings, and errors that are used to manage, understand, improve, and debug in the logging data repository 431. Logging data includes data such as system diagnostics, software and hardware versions, and observations of the system under normal use and exceptional situations or failures. Similarly, the logging and telemetry logic 402 interacts with a (in some embodiments external) telemetry services 435 to collect and log telemetry data in the telemetry data repository 436. Telemetry data includes data such as system activation, active usage, positioning activations, and pressure monitoring. Telemetry data is used to observe and report on the posture changes and pressure observations relative to the end user of the device. Telemetry is of interest, for example, to the person using the device, the manufacturer of the powered seating device, the assistive technology clinicians who recommend the device, and the medical practitioners responsible for advising the person on health and injury matters. Components such as the logging service 430, the telemetry service 435 and other applications interface with the EGPCS 400 via network 420, e.g., a wide area network such as the Internet or a local area network.

The posture control application 403 is responsible for directly interacting with the user via eye gaze technology to select which aspect of the powered wheelchair/bed is to be adjusted and in what way, for example, degree of angular rotation. Application 403 is the heart of the EGPCS 400 and, in some examples EGPCS 400, interacts with the posture and pressure advisor 401 to prevent injury which can occur due to lack of blood flow due to long term pressure restrictions from lack of movement.

The posture and pressure advisor 401 applies rules and best practices to offer automated recommendations to the device (e.g., wheelchair/bed) user and their caregivers to maintain comfort and prevent injuries such as pressure sores. This can be especially helpful for people who are either unable to communicate their needs and feelings, such as people with motor-neuron diseases which impact effective communications, or for people who are unable to feel when pressure sores are beginning to form, such as people with spinal cord or traumatic brain injury. In some EGPCS, when a rule or pressure monitor observation results in a posture change recommendation, the person and/or caregiver is notified of the recommendation to make a posture change. If a recommendation is made and a posture change is not detected within a reasonable period, the telemetry service 435 may be used to notify a caregiver or record the lack of action.

Device interface(s) 404 interact with the various posture controllers and actuators 410, pressure monitors 411, and other I/O devices 412 to cause the wheelchair/bad to move according to the end user selections. Example of such interfaces include the Permobil Corpus Seating System ("https://www.permobil.com/en-us/products/power-wheelchairs/functions/corpus-seating-system"), Linak HB22 linear actuator ("https://cdn.linak.com/-/media/files/user-manual-source/en/homeline-twindrive-td1-220-250-user-manual-eng.pd/"), and Drive Delta 1000 Hospital Bed, and Curtis-Wright RNet Power Module ("https://www.cwindustrialgroup.com/Products/Mobility-Vehicle-Solutions/R-net/Standard-Power-Module"). There may be an intermediary position controller which acts as a translation device between the tablet computer's USB port and the powered seating actuator which may use simple physical switch input (e.g., normally open switches) or a low-level microcontroller optimized protocol such as RS-422, RS-232, or CAN Bus.

In some example EGPCSes 400, certain posture control and configuration data 406 is also stored in a data repository. Such data may aid in configuration defaults, stored end user information available to the posture and pressure advisor 401, and the like.

Figure 5:
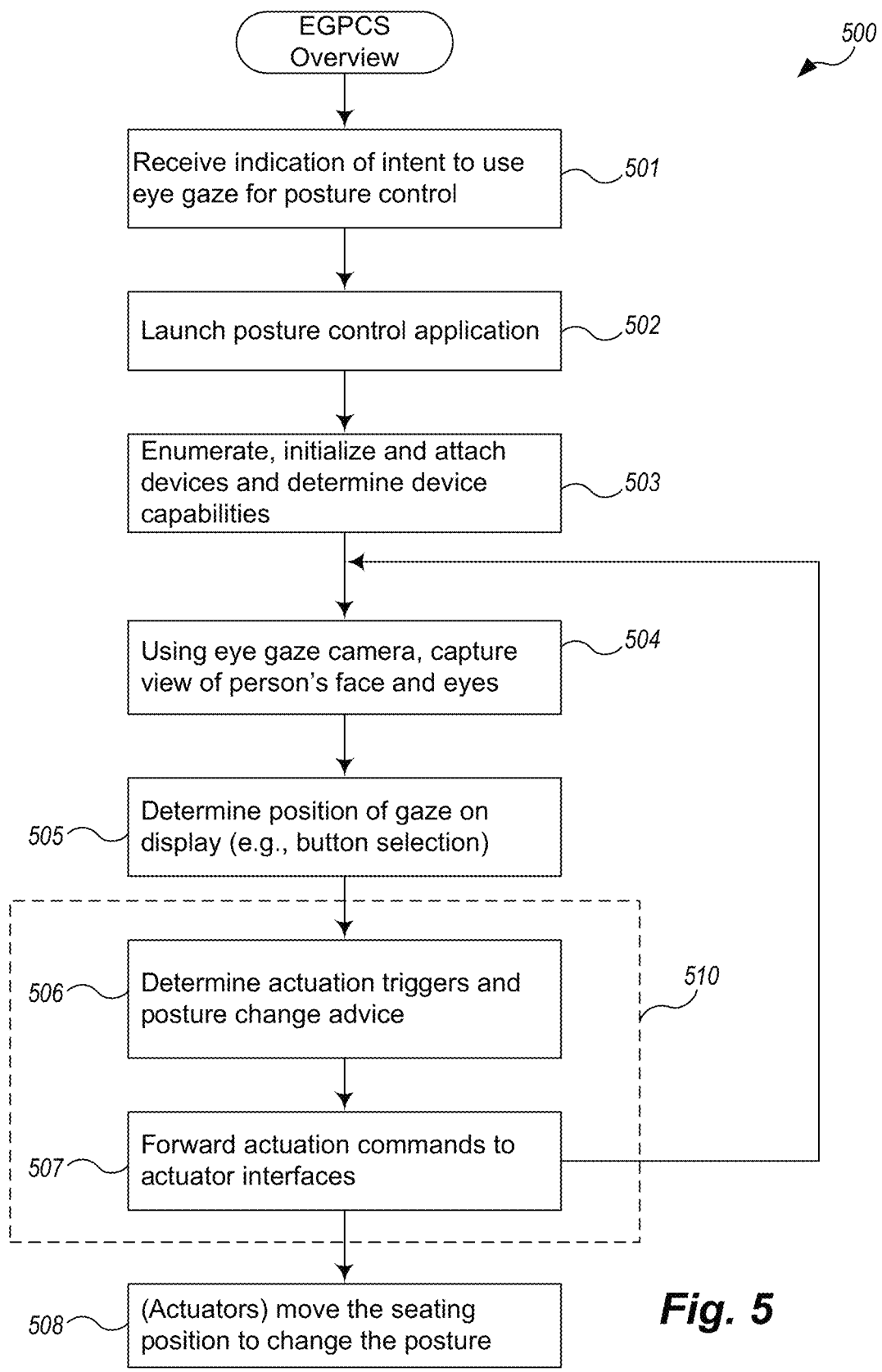
FIG. 5 is an overview flow diagram of an example Eye Gaze Posture Control System used to control adjustable positioning.

FIG. 5 is an overview flow diagram of an example Eye Gaze Posture Control System used to control adjustable positioning. An example EGPCS, such as EGPCS 400 of FIG. 4, is responsible for interfacing with an end user to provide improved self-control of powered devices via eye gaze technology to adjust aspects such as, in a powered wheelchair, vertical control of the seat (lift), the angle of the legs, the angle of the back rest (the recline angle), and the angle of the chair to the base (tilting), and the like. The various components of the EGPCS 400 shown in FIG. 4 interact to achieve these adjustments. The EGPCS may be part of a larger eye gaze system which provides other functions such as controlling a computer or web browser, speaking, driving a powered wheelchair, and the like.

More specifically, in block 501, the EGPSC receives an indication of (an end user's) intent to user eye gaze for posture control. This indication may come in a variety of forms and from a variety of scenarios, dependent upon how the EGPCS is integrated into a new or existing powered wheelchair/bed. Example integrations are described further below with respect to FIGS. 6-8.

In block 502, the EGPCS launches a posture control application to interface with the end user using eye gaze technology. An example posture control application is described further below with respect to FIGS. 10-13. The posture control application allows the user to select an axis of movement to adjust and the specifics of the adjustment using eye gaze technology without any need to involve additional sources of input such as from a virtual mouse or keyboard or from a caregiver. As explained above, this results in enhanced freedom to the severely disabled end user.

In block 503, the EGPCS engages in a discovery and connection process to attach various devices (such as devices 410-412 shown in FIG. 4) used to control posture adjustments. Example devices for possible enumeration are described below with reference to FIG. 9. The logic of block 503 may be accomplished by using known technology such as USB device discovery, Ethernet & Link Level Discovery Protocol, Internet Protocol Multicast DNS, Bluetooth, WiFi, etc.

In block 504, the EGPCS uses eye gaze camera(s) 210 to capture the end user's face and eyes. This input is used in block 505 to determine a position of the gaze of the end user, for example, which user interface control (e.g., button) is being indicated as selected. Examples of eye gaze capture technology that may be incorporated for this logic include Tobii IS5 based eye trackers, devices from EyeTech Digital Systems, RGB eye tracking such as WebGaze from Brown University, and the like.

In block 506 the EGPCS determines which actuation controls are being triggered by the end user through an eye gaze selection interface and whether the posture and pressure advisor is recommending something different other than what the end user has selected. In some example EGPCS implementations, the advisor recommendations are automatically executed by the computing system executing the EGPCS to prevent the user from adjusting his/her posture into a position that could be harmful. In other example EGPCS implementations, the advisor recommendations are considered just that—recommendations—and the end user is presented with the information and an ability to accept or override the recommendations. Other combinations are possible as well.

In block 507, once the posture adjustment has been effectuated, the EGPCS forwards commands to the actuators to cause the chair/bed to move according to the end user selections. Blocks 506 and 507 (510) are executed as part a posture control application, described further below with respect to FIG. 10.

In block 508, the actuators, upon receiving commands from the posture control application, move the seating/bed position appropriately to change posture.

Figure 6:
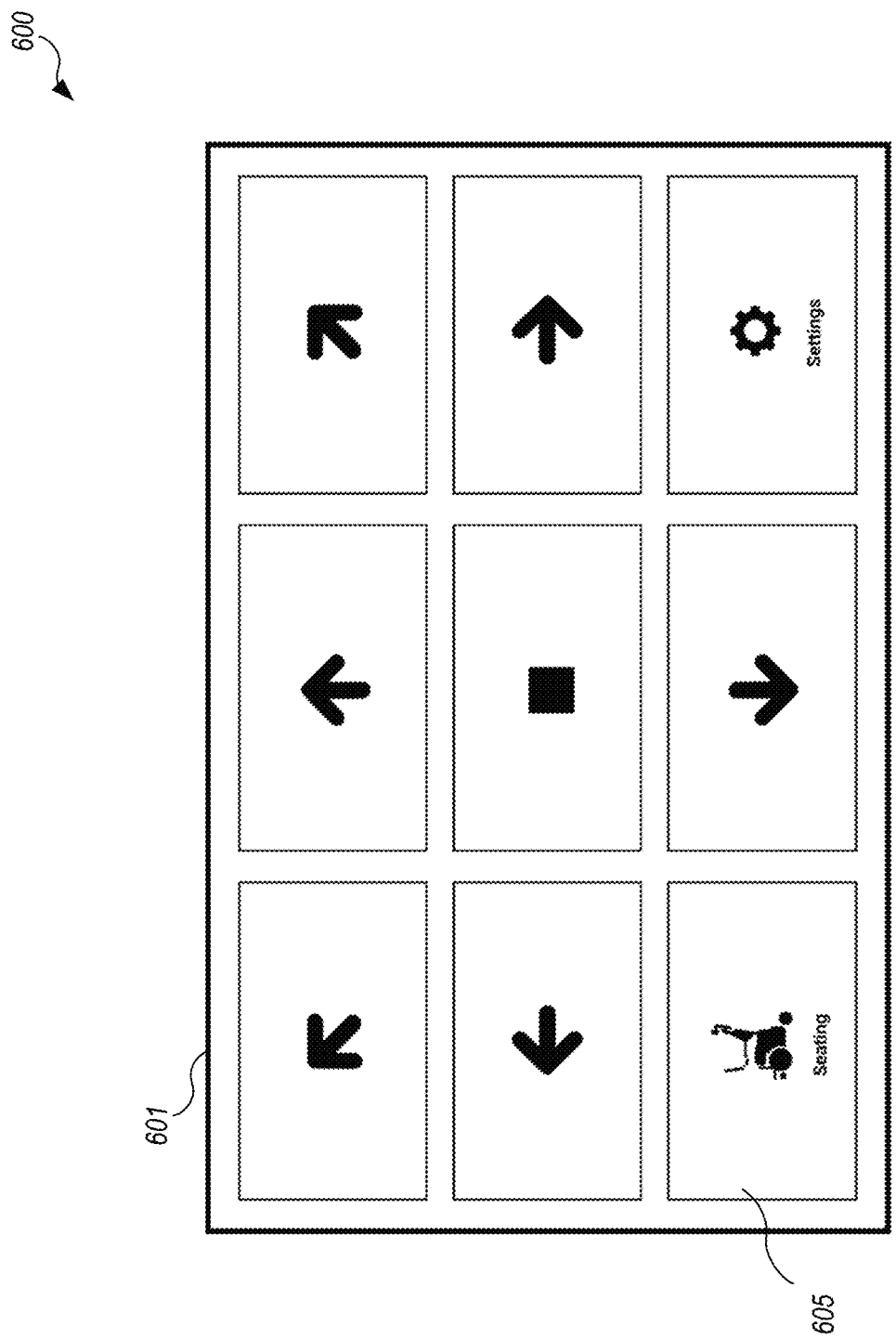
FIG. 6 is an example screen display of a user interface from which an example Eye Gaze Posture Control System is executed.

FIG. 6 is an example screen display of a user interface from which an example Eye Gaze Posture Control System is executed. Example screen display 600 shows an interface 601 currently available in the market from Tolt Technologies, called "Ability Drive." The EGPCS is integrated into the user interface of Ability Drive through a user interface control 605, labeled "seating." This button 605 is selectable through eye gaze recognition and interaction technology as described above and is used to advance the user to a posture adjustment selection user interface as described below with respect to FIGS. 11 and 12. The other eye gaze selectable buttons shown with directional arrows are used for driving the wheelchair.

Figure 7:
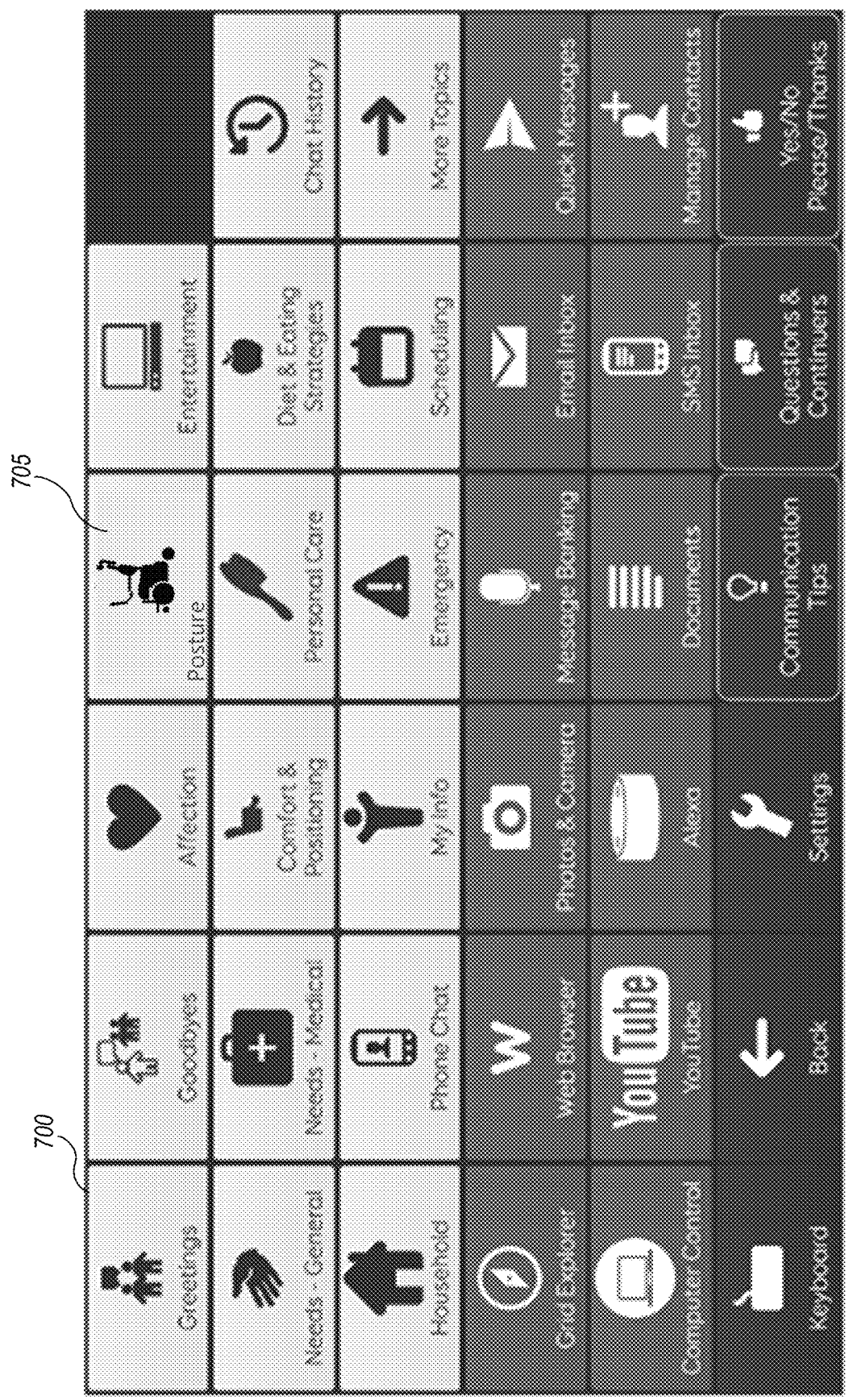
FIG. 7 is an example screen display of integration within a third-party user interface from which an example Eye Gaze Posture Control System can be invoked.

FIG. 7 is an example screen display of integration within a third-party user interface from which an example Eye Gaze Posture Control System can be invoked. Display screen 700 shows Grid 3 software from SmartBox Assistive Technology Ltd. The EGPCS is integrated into interface 700 by adding a tile 705 to the display screen 700 of applications and utilities for a variety of personal needs which are eye gaze navigable.

Figure 8:
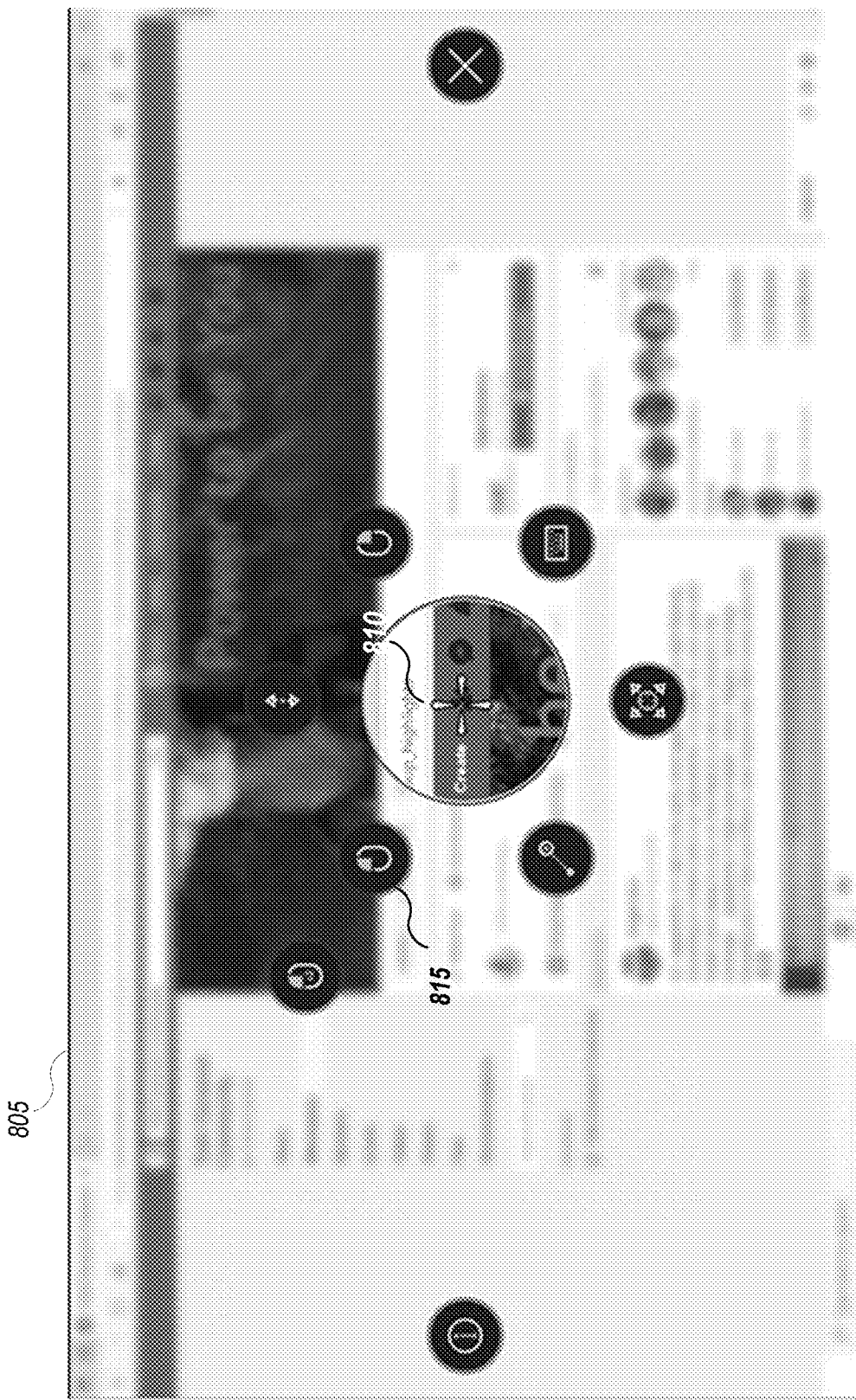
FIG. 8 is an example screen display of integration with an eye gaze controlled virtual mouse from which an example Eye Gaze Posture Control System can be invoked.

FIG. 8 is an example screen display of integration with an eye gaze controlled virtual mouse from which an example Eye Gaze Posture Control System can be invoked. In this example, a Tobii Computer Control system 805 uses eye gaze to simulate moving and clicking a mouse on the Windows Desktop to interact with an application display screen 805. This same approach can be used to launch an EGPCS via a Windows shortcut to the application.

Figure 9:
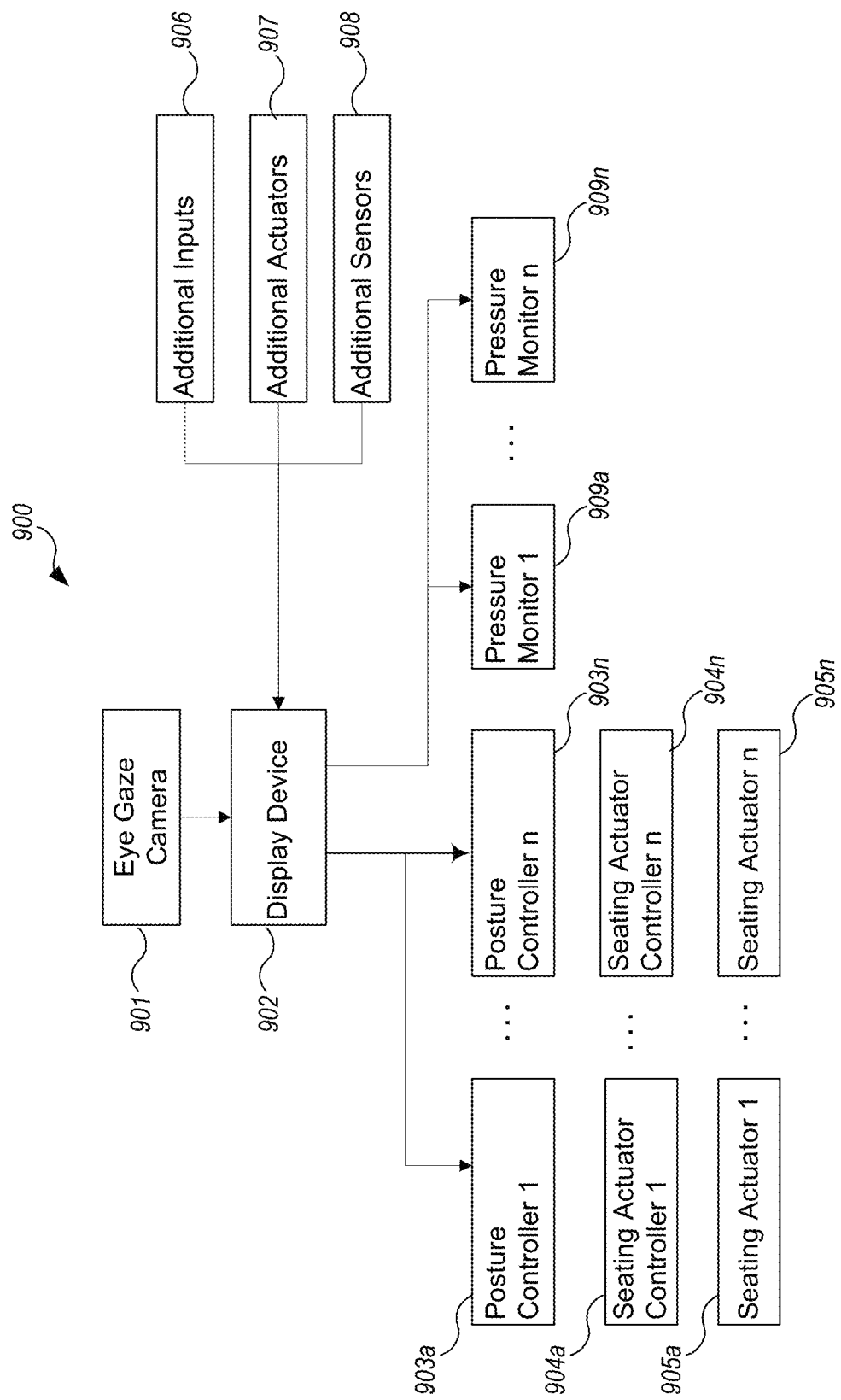
FIG. 9 is an example block diagram of devices available for enumeration and attachment by an example Eye Gaze Posture Control System.

FIG. 9 is an example block diagram of devices available for enumeration and attachment by an example Eye Gaze Posture Control System. For example, in block 503 of FIG. 5, the EGPCS engages in a discovery and connection process to attach one or more of the devices shown in FIG. 9, which may be connected to any particular wheelchair/bed/chair. The devices available to be enumerated, attached, and initiated may include one or more eye gaze cameras 901, display devices 902, posture controllers 903*a*-903*n*, seating actuator controllers 904*a*-904*n*, and seating actuators 905*a*-90*g*, pressure monitors 909*a*-909*n* depending upon the subject wheelchair/bed.

The display device(s) 902 may take many forms such as: a tablet PC like a Microsoft Surface Pro, Apple iPad, or Android Tablet; a phone like an Android phone or Apple iPhone or other smartphone; a dedicated display such as an LCD or LED monitor or similar display device; or a head mounted display such as AR (Augmented Reality) glasses or VR (Virtual Reality) googles. The eye gaze display 902 may take the form of a computer system which runs an operating system with additional eye gaze interaction software enhancements. These enhancements can take the form of input simulation (e.g., a virtual mouse, such as displayed in FIG. 8) or an eye gaze enhanced navigation experience (e.g., eye gaze enabled grids of buttons, such as displayed in FIG. 7, or integrated with a powered wheelchair driving app, for example displayed in FIG. 6). In some example embodiments, such as a hospital bed in a hospital room (e.g., FIG. 3), the operating system may run in a background and the positioning app may be run as a dedicated application on the device, for example in a "kiosk mode". In other embodiments, the positioning app may be part of a larger, more wholistic system that includes other functionality, such as speech generation assistance, environmental control, powered wheelchair movement control, etc. In this case, the operating system with eye gaze interaction is used to navigate between the positioning app and the other assistive functionalities of the eye gaze enabled display.

The eye gaze camera(s) 901 may be a 'smart camera' which includes an image capture device, a light emitter, and optionally an image or geometric co-processor; a 'RGB or infrared or web' camera, which is simply an image capture device which relies on a separate CPU, perhaps integrated with the display device or attached elsewhere in the system; a series of cameras mounted in the AR/VR display; or one or more cameras mounted on our around the environment, separate from the display 902.

Posture controllers 903*a*-903*n* comprise one or more "bridge" devices that connect the display device (902) to the seating actuation controller(s) (904*a*-904*n*). Since many seating actuation controller(s) (904*a*-904*n*) are designed to be activated using manual buttons via a remote control (e.g., FIG. 1), the seating actuation controller(s) (904*a*-904*n*) can take the form of a USB or Bluetooth device which communicates with the operating system/I/O system of the display device(s) 902 and provides a protocol to actuate by acting as normally open switches (the common physical implementation of the manual buttons on the remote control). This may be implemented using a physical relay switch device, a solid-state relay, or an opto-isolated solid-state relay. The seating actuation controller(s) (904*a*-904*n*) are provided as part of the motorized bedding or seating manufacturer and are generally implemented as a motor controller that takes AC or DC power, handles one or more motors or linear actuators (seating actuators 905*a*-905*n*), and has an input system which may consist of a hard-wired button controller or a control port such as an RJ11 jack or DB9 port. These seating actuators 905*a*-905*n* may be implemented as AC or DC motors but are not limited to these, as other options such as pneumatic, hydraulic, or other variations actuator movement many be implemented.

The EGPCS may also include one or more pressure monitors 909*a*-909*n* which are used to monitor for potential issues with discomfort or the development of pressure sores. Pressure monitors 909*a*-909*n* typically have an array of pressure sensors which measure mmHg of pressure which are then observed over a period of time.

Additional inputs 906, actuators 907, and sensors 908 may similarly be integrated into a wheelchair/bed and also available to be controlled. For example, they may include switches used to provide additional input control (e.g., selection or mouse clicks), combinations or arrays of inputs to maximize the independent control of partial disabilities (e.g., eye gaze plus click), speech recognition (e.g., "lift legs"), muscle tensing/nerve actuation (e.g. EMI or EEG) sensors, brainwave detection (e.g., BCI) sensors, etc. Additional actuators 907 could control other aspects of movement, such as wheelchair motion control, camera control such as pan/tilt/zoom, camera selection such as 'forward view camera' & 'rear view camera', head/neck support control such as 'tilt head forward/tilt head back', etc. Additional sensors 908 may include cameras, button switches, EMG muscle sensors, brain control interface sensors, etc.

Figure 10:
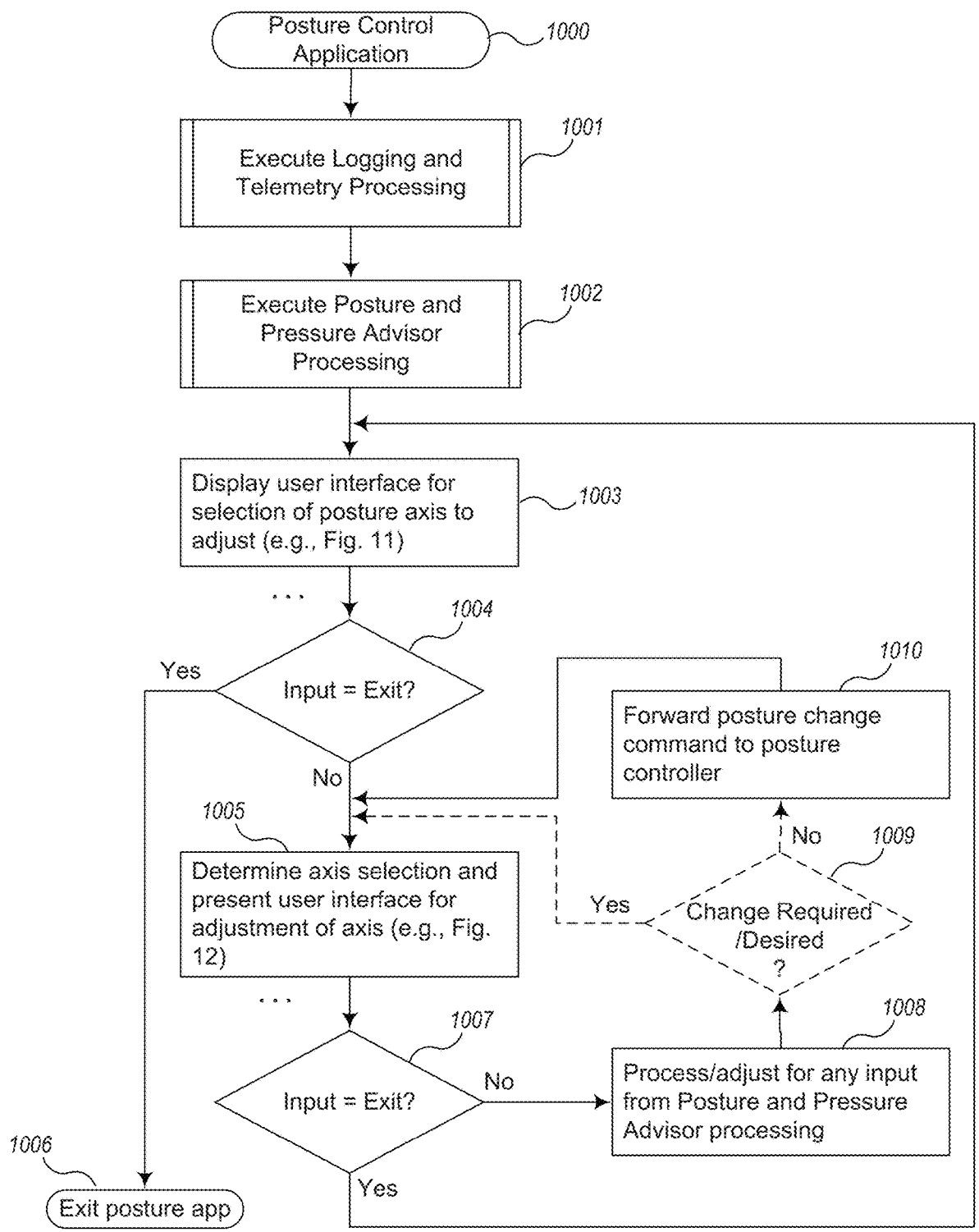
FIG. 10 is an example flow diagram of an example posture control application logic of an example Eye Gaze Posture Control System.

FIG. 10 is an example flow diagram of an example posture control application logic of an example Eye Gaze Posture Control System. Example posture control application 1000 includes logic to enable an end user to set and adjust various components of the wheelchair/bed that affect posture. This logic may be invoked by an example EGPCS such as EGPCS 400 in FIG. 4, for example in block 502 in FIG. 5. Although shown sequentially it will be appreciated that various logic statements may be executed asynchronously and in different orders and can be modified as desired to incorporate additional logic.

In block 1001, the posture control application logic executes logging and telemetry processing. In example EGPCS applications, this processing is performed concurrently (e.g., in a different process/thread, etc.) so that continuous logging may occur. This logging enables diagnostics of application health and performance, feedback on application usage, and feature utilization. The telemetry processing enables recording data on system sensor measurements and usage, such as recording time spent in chair, pressure measurement observations, movement frequency and duration, time spent in various positions (e.g. reclined, upright), etc.

In block 1002, the posture control application logic executes posture and pressure advisor processing. The posture and pressure advisor processing is described further below with respect to FIG. 13 and is responsible for monitoring the position of the end user so that adjustments to the wheelchair/bed do not result in inadvertent dangers or health issues. In example EGPCS applications, this processing is performed concurrently (e.g., in a different process/thread, etc.) so that continuous advising may occur.

Figure 11:
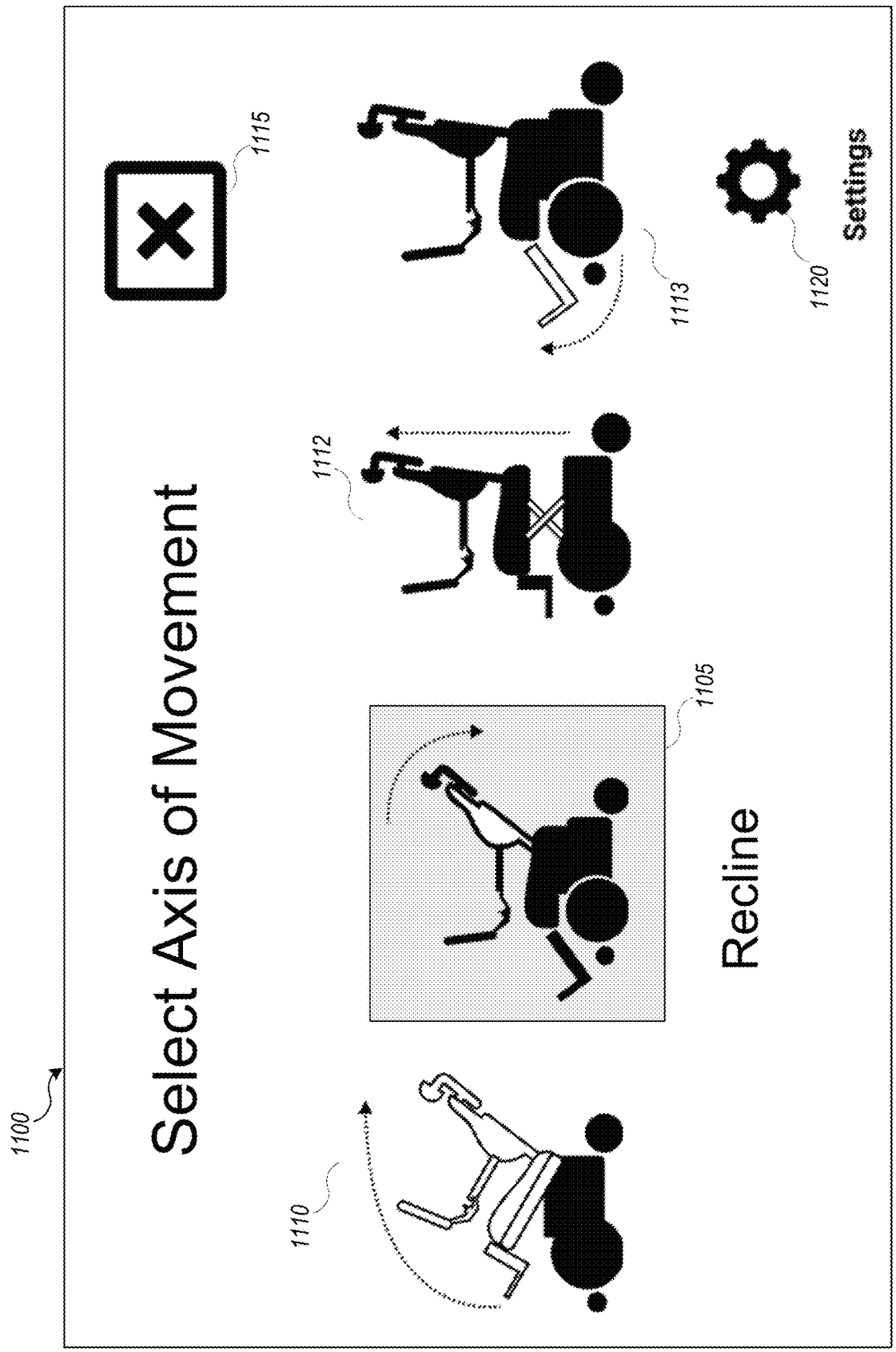
FIG. 11 is an example screen display of a user interface for selection of an axis for adjustment in an example Eye Gaze Posture Control System.

In block 1003, the logic displays a user interface for the end user to select a posture axis to adjust. In one example EGPCS, these axes include leg lift, upper torso recline, seat tilt, seat height, head tilt, head pan, etc. FIG. 11 is an example screen display of a user interface for selection of an axis for adjustment in an example Eye Gaze Posture Control System such as that indicated in block 1003. A set of choices for which axis to control is presented and one axis is activated (e.g., selected). As seen in example screen display 1100, the end user may select an exit icon 1115, tilting the body (icon 1110), reclining the torso/head (icon 1105), raising the chair/bed height (icon 1112), or a lifting the feet/legs (icon 1113). Other buttons may be available such as for lifting the head/chin, turning the head, and the like. The settings icon 1120 allows the end user to configure the posture control application through a configuration interface. For example, the configuration interface may be used to adjust the user experience (such as selection times, color pallets, etc.) and to create 'preset positions' for a combination of posture axis position targets, such as 'resting' (e.g., back mostly reclined, legs lifted), 'talking' (e.g., sitting up, head reclined slightly), 'driving' (e.g., body straight, head looking directly forward), etc. The screen display 1100 may include choices and selection buttons for these preset positions, not displayed here. A button is selected from screen display 1100 by gazing at the button for a period of time. In one EGPCS, the selected axis is highlighted to the user through a change in color, background, bounding box, etc.

Once the end user selects (e.g., using eye gaze recognition and control) a user interface control (e.g., a virtual button) from the interface (e.g., as illustrated in FIG. 11), then in block 1004, the logic determines whether the input indicates an intent to "exit" the posture control application, and, if so, continues in block 1006 to exit the application. Otherwise, the logic continues in block 1005.

Figure 12:
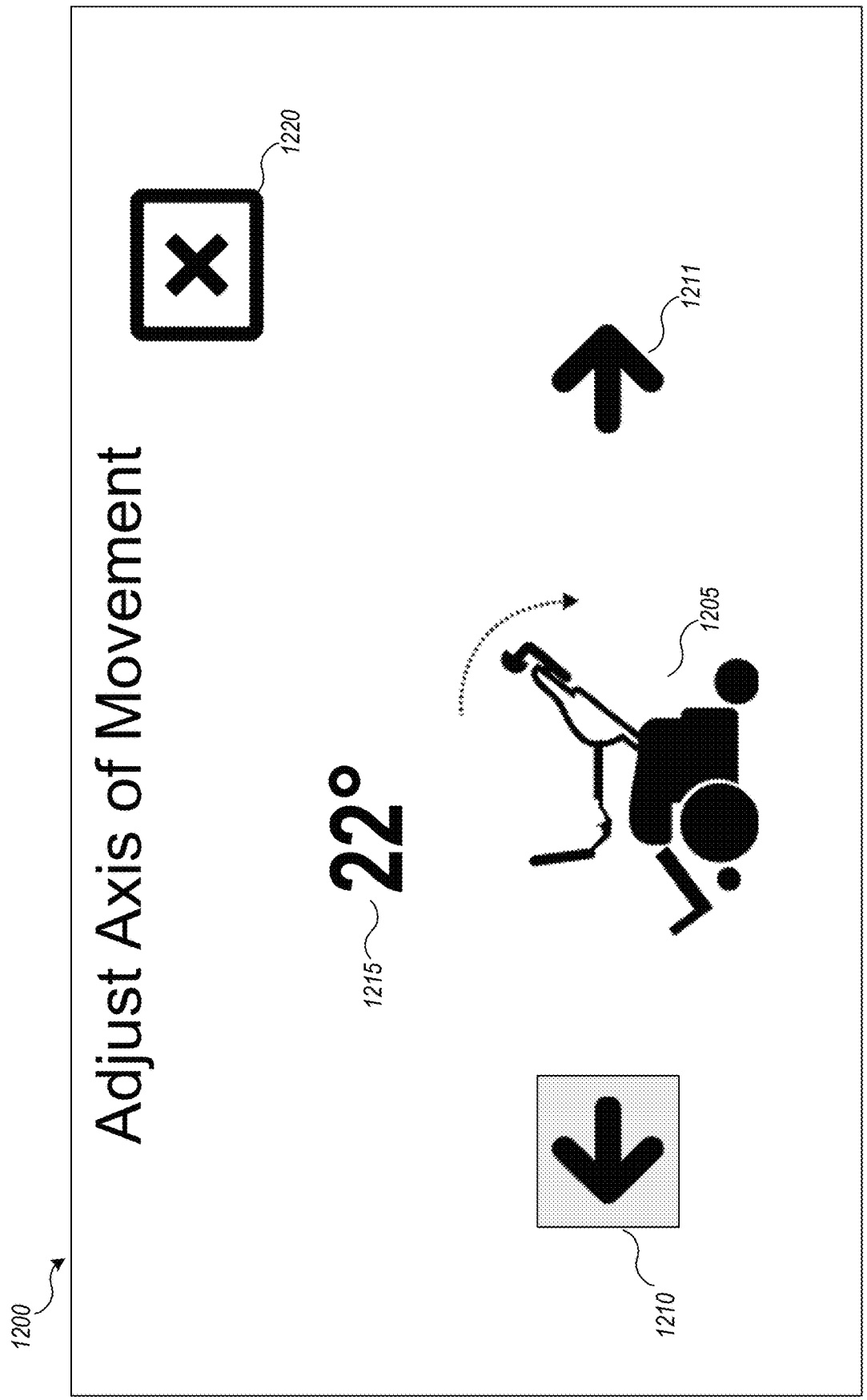
FIG. 12 is an example screen display of a user interface for adjusting an axis of movement in an example Eye Gaze Posture Control System.

In block 1005, the logic determines which axis the end user selected (e.g., in FIG. 11) and presents a secondary interface for the user to indicate a particular adjustment for that axis. FIG. 12 is an example screen display of a user interface for adjusting an axis of movement in an example Eye Gaze Posture Control System. In the example screen display 1200 illustrated, the axis previously selected in FIG. 11 is displayed for reference 1205 and two arrow buttons left 1210 and right 1211 provide the user choice in the change of axis position. The current measured position (status) of the axis 1215 may be displayed in appropriate units, provided that the seating actuator controller can measure position and communicate state back to the EGPCS. The exit button 1220 can be used to exit this screen and return to the axis selection screen 1100, for example as shown in FIG. 11.

Of note, the first and secondary interfaces may be presented at the same time (e.g., without shifting to a new display screen as shown in FIGS. 11 and 12). Other configurations including sharing a display screen and presenting the adjustment user interface controls once an axis is selected also can be similarly incorporated.

Once the end user selects (using eye gaze recognition and control) a user interface control (e.g., a button) from the interface (e.g., as illustrated in FIG. 12), then in block 1007 the logic determines whether the input indicates an intent to "exit" the adjustment screen, and if so continues in block 1003 to go back to selected an axis to adjust (e.g., FIG. 11). Otherwise, the logic continues in block 1008.

In block 1008, the logic determines and process any input received (e.g., asynchronously, for example through messages, event registration, or the like) from the posture and pressure advisor ("posture advisor") processing. In one example EGPCS, the logic determines in block 1009 if the posture advisor is suggesting a change to the user selections and if so, returns the user to the interface for adjusting the axis (e.g., FIG. 12) for further adjustments. Along with this, the logic may present information to the user from the posture advisor to improve decisions. In some EGPCS embodiments, the logic overrides the user automatically and adjusts the wheelchair/bed without user intervention to prevent dangerous situations or health problems. In other embodiments the posture advisor recommendations may be shown or ignored or overridden by the user and the logic continues in block 1010.

If the posture advisor does not indicate any change is recommended or desired, or if it is overridden, then the logic proceeds to block 1010 to forward posture change commands that correspond to the end user's selections to the appropriate posture controller. The logic then returns to block 1005 to process the user interface display for further adjustments (e.g., FIG. 12). In other embodiments, the logic may proceed to other blocks such as block 1003 or to block 1006 to exit the application.

Figure 13:
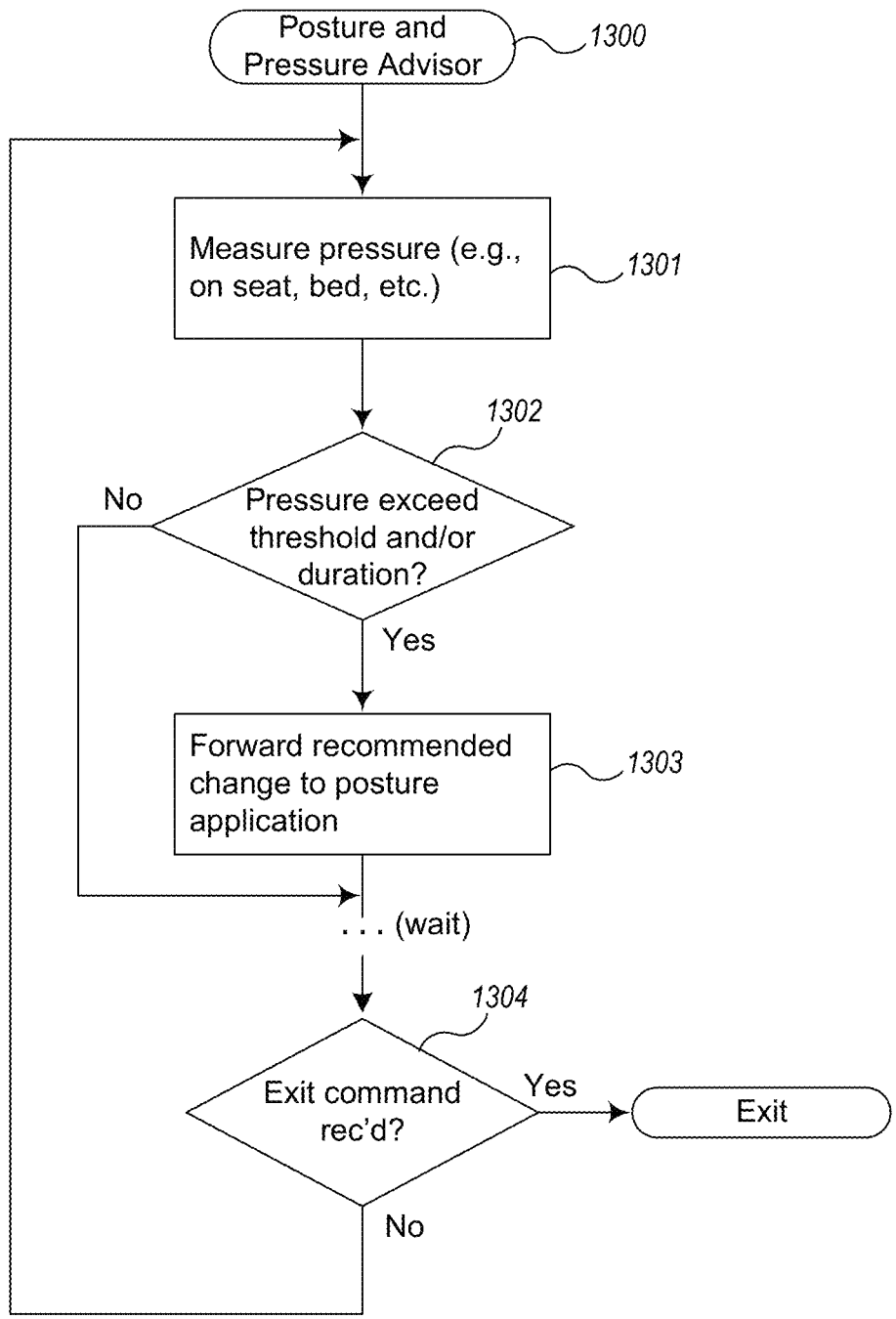
FIG. 13 is an example flow diagram of an example posture and pressure advisor logic for measuring and forwarding recommendations in an example Eye Gaze Posture Control System.

FIG. 13 is an example flow diagram of an example posture and pressure advisor logic for measuring and forwarding recommendations in an example Eye Gaze Posture Control System. The posture and pressure advisor logic may be executed, for example, by posture and pressure advisor 401 in FIG. 4. The pressure and posture observation system provides advice for changing posture to help reduce the probability of developing discomfort or ulcers (e.g., bed sores). Specifically, in block 1301, the posture and pressure advisor logic 1300 measures pressure, for example, by means of the pressure monitors 230 described with reference to FIG. 2. In block 1302, the log determines whether the pressure has exceeded a (potentially configurable) threshold and/or duration, and, if so, continues in block 1303, else continues to a wait for some period of time (also potentially configurable) until the logic resumes in block 1304. In block 1303, the logic forwards a recommended change to the posture application (e.g., application 1000 in FIG. 10), which as explained there can provide recommendations, overrides, etc. In block 1304, after a timeout period, the logic resumes to determine whether the user has indicated an exit command. If so, the advisor logic exits, and, if not, the advisor logic returns to measure pressure in block 1301.

The techniques of Eye Gaze Posture Control System are generally applicable to any type of device that a user can occupy and that can be controlled to change the user's position in the device, for example by tilting, raising, lowering, etc. Also, although the examples described herein often refer to a powered wheelchair, the techniques described herein can also be used in beds, cars, and other transportation devices. Also, although certain terms are used primarily herein, other terms could be used interchangeably to yield equivalent embodiments and examples. In addition, terms may have alternate spellings which may or may not be explicitly mentioned, and all such variations of terms are intended to be included.

Example embodiments described herein provide applications, tools, data structures and other support to implement Eye Gaze Posture Control System to be used to control seating and lying posture through eye gaze control. Other embodiments may incorporate the use of brain-computer interface (BCI) technologies to provide input instead of or in addition to using eye gaze control. BCI technologies are described further in Nicolas-Alonzo and Gomez-Gil, "Brain Computer Interfaces, A Review," Department of Signal Theory, Communications and Telematics Engineering, University of Valladolid, Valladolid 47011, Spain, "https://www.ncbi.nlm.nih.gov/pmc/articles/PMC3304110/pdf/sensors-12-01211.pdf," which is herein incorporated by reference in its entirety. An example BCI device is the Emotive Insight 5 headset, available at "https://www.emotiv.com/insight/." Similarly, other embodiments may incorporate the use of EMG (electromyography) technology to provide input instead of or in addition to using eye gaze control. EMG technologies are described further in Lee et al., "Biological Surface Electromyographic Switch and Necklace-type Button Switch Control as an Augmentative and Alternative Communication Input Device: A Feasibility Study," *Australasian Physical & Engineering Sciences in Medicine*, Vol. 42(5), June 2019, which is herein incorporated by reference in its entirety. An example EMG switch implementation is NeuroNode by Control Bionics, available at "https://www.controlbionics.com/products/."

Other embodiments of the described techniques may be used for other purposes. In the following description, numerous specific details are set forth, such as data formats and code sequences, etc., in order to provide a thorough understanding of the described techniques. The embodiments described also can be practiced without some of the specific details described herein, or with other specific details, such as changes with respect to the ordering of the logic, different logic, etc. Thus, the scope of the techniques and/or functions described are not limited by the particular order, selection, or decomposition of aspects described with reference to any particular routine, module, component, and the like.

Figure 14:
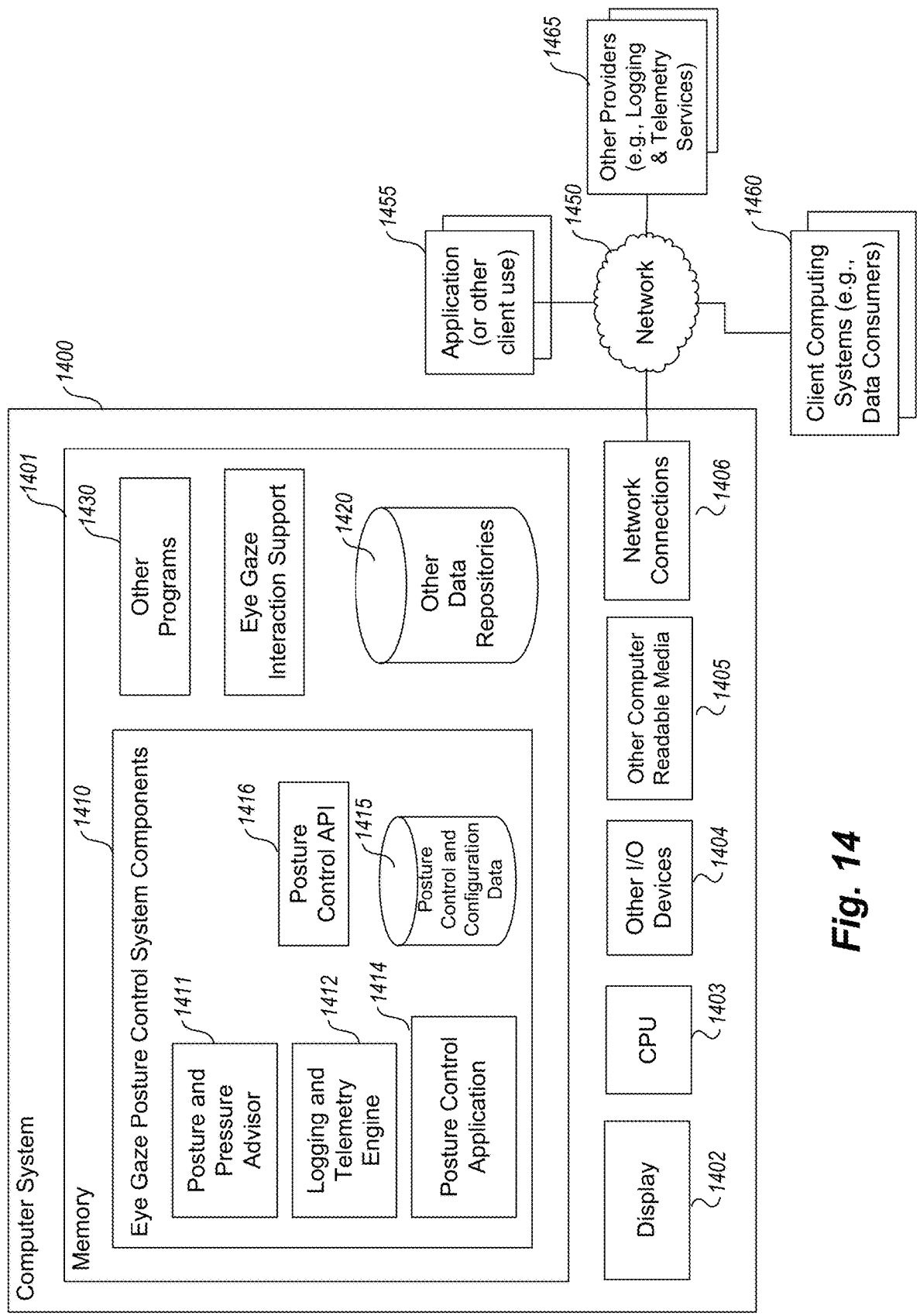
FIG. 14 is an example block diagram of a computing system for practicing embodiments of an Eye Gaze Posture Control System.

FIG. 14 is an example block diagram of a computing system for practicing embodiments of an Eye Gaze Posture Control System described herein. Note that one or more general purpose virtual or physical computing systems suitably instructed or a special purpose computing system may be used to implement an EGPCS. Further, the EGPCS may be implemented in software, hardware, firmware, or in some combination to achieve the capabilities described herein.

Note that one or more general purpose or special purpose computing systems/devices may be used to implement the described techniques. However, just because it is possible to implement Eye Gaze Posture Control System on a general purpose computing system does not mean that the techniques themselves or the operations required to implement the techniques are conventional or well known.

The computing system 1400 may comprise one or more server and/or client computing systems and may span distributed locations. In addition, each block shown may represent one or more such blocks as appropriate to a specific embodiment or may be combined with other blocks. Moreover, the various blocks of the EGPCS 1410 may physically reside on one or more machines, which use standard (e.g., TCP/IP) or proprietary interprocess communication mechanisms to communicate with each other.

In the embodiment shown, computer system 1400 comprises a computer memory ("memory") 1401, a display 1402, one or more Central Processing Units ("CPU") 1403, Input/Output devices 1404 (e.g., keyboard, mouse, CRT or LCD display, etc.), other computer-readable media 1405, and one or more network connections 1406. The EGPCS components 1410 is shown residing in memory 1401. In other embodiments, some portion of the contents, some of, or all of the components of the EGPCS 1410 may be stored on and/or transmitted over the other computer-readable media 1405. The components of the EGPCS 1410 preferably execute on one or more CPUs 1403 and manage the posture control using eye gaze technology, as described herein. Other code or programs 1430 and potentially other data repositories, such as data repository 1420, also reside in the memory 1401, and preferably execute on one or more CPUs 1403. Of note, one or more of the components in FIG. 14 may not be present in any specific implementation. For example, some embodiments embedded in other software may not provide means for user input or display.

In a typical embodiment, the EGPCS 1410 includes one or more posture and pressure (or other) advisors 1411 (as described with reference to FIG. 13), one or more logging and telemetry engines 1412, and a posture control application 1414 (as described with reference to FIG. 10). In addition, the EGPCS 1410 may store posture control and configuration data 1415, for example specific to a particular user or configuration. In at least some embodiments, the logging and telemetry engine 1412 is provided external to the EGPCS and is available, potentially, over one or more networks 1450. Other and/or different modules may be implemented. In addition, the EGPCS may interact via a network 1450 with application or client code 1455, for example a healthcare worker monitoring application that uses results computed by the EGPCS, one or more client computing systems 1460, for example those that use the data provided by the logging and telemetry engine 1412, and/or one or more third-party information provider systems 1465, such as third-party logging and telemetry services. Also, of note, the posture control and configuration data repository 1415 may be provided external to the EGPCS as well, for example in a data repository accessible over one or more networks 1450.

For example, one potential client computing system 1460 may be a data consumer that forwards/consumes telemetry data which is bridged into a larger electronic medical records system. Another data consumer 1460 or client application 1455 could be a private secured portal for the person and their caregivers. Another data consumer 1460 could be a notification system that sends suggestions or alerts to the person or their caregivers to assist with repositioning monitoring and needs. Telemetry services 1465 could be consumed by the manufacturer of the system to understand system usage, diagnostics, and provide support or by the owner of the system, an assisted living facility, or a hospital IT staff.

In an example embodiment, components/modules of the EGPCS 1410 are implemented using standard programming techniques. For example, the EGPCS 1410 may be implemented as a "native" executable running on the CPU 103, along with one or more static or dynamic libraries. In other embodiments, the EGPCS 1410 may be implemented as instructions processed by a virtual machine. A range of programming languages known in the art may be employed for implementing such example embodiments, including representative implementations of various programming language paradigms, including but not limited to, object-oriented, functional, procedural, scripting, and declarative.

The embodiments described above may also use well-known or proprietary, synchronous or asynchronous client-server computing techniques. Also, the various components may be implemented using more monolithic programming techniques, for example, as an executable running on a single CPU computer system, or alternatively decomposed using a variety of structuring techniques known in the art, including but not limited to, multiprogramming, multi-threading, client-server, or peer-to-peer, running on one or more computer systems each having one or more CPUs. Some embodiments may execute concurrently and asynchronously and communicate using message passing techniques. Equivalent synchronous embodiments are also supported.

In addition, programming interfaces 1416 to the data stored as part of the EGPCS 1410 (e.g., in the data repositories 1415) can be available by standard mechanisms such as through C, C++, C#, and Java APIs; libraries for accessing files, databases, or other data repositories; through scripting languages such as XML; or through Web servers, FTP servers, or other types of servers providing access to stored data. The data repository 1415 may be implemented as one or more database systems, file systems, or any other technique for storing such information, or any combination of the above, including implementations using distributed computing techniques.

Also, the example EGPCS 1410 may be implemented in a distributed environment comprising multiple, even heterogeneous, computer systems and networks. Different configurations and locations of programs and data are contemplated for use with techniques of described herein. In addition, the components may be physical or virtual computing systems and may reside on the same physical system. Also, one or more of the modules may themselves be distributed, pooled, or otherwise grouped, such as for load balancing, reliability or security reasons. A variety of distributed computing techniques are appropriate for implementing the components of the illustrated embodiments in a distributed manner including but not limited to TCP/IP sockets, RPC, RMI, HTTP, Web Services (XML-RPC, JAX-RPC, SOAP, etc.) and the like. Other variations are possible. Also, other functionality could be provided by each component/module, or existing functionality could be distributed amongst the components/modules in different ways, yet still achieve the functions of an EGPCS.

Furthermore, in some embodiments, some or all of the components of the EGPCS 1410 may be implemented or provided in other manners, such as at least partially in firmware and/or hardware, including, but not limited to one or more application-specific integrated circuits (ASICs), standard integrated circuits, controllers executing appropriate instructions, and including microcontrollers and/or embedded controllers, field-programmable gate arrays (FPGAs), complex programmable logic devices (CPLDs), and the like. Some or all of the system components and/or data structures may also be stored as contents (e.g., as executable or other machine-readable software instructions or structured data) on a computer-readable medium (e.g., a hard disk; memory; network; other computer-readable medium; or other portable media article to be read by an appropriate drive or via an appropriate connection, such as a DVD or flash memory device) to enable the computer-readable medium to execute or otherwise use or provide the contents to perform at least some of the described techniques. Some or all of the components and/or data structures may be stored on tangible, non-transitory storage mediums. Some or all of the system components and data structures may also be stored as data signals (e.g., by being encoded as part of a carrier wave or included as part of an analog or digital propagated signal) on a variety of computer-readable transmission mediums, which are then transmitted, including across wireless-based and wired/cable-based mediums, and may take a variety of forms (e.g., as part of a single or multiplexed analog signal, or as multiple discrete digital packets or frames). Such computer program products may also take other forms in other embodiments. Accordingly, embodiments of this disclosure may be practiced with other computer system configurations.

All of the above U.S. patents, U.S. patent application publications, U.S. patent applications, foreign patents, foreign patent applications and non-patent publications referred to in this specification and/or listed in the Application Data Sheet, including but not limited to U.S. Provisional Patent Application No. 63/088,451, entitled "Systems and Methods for Controlling Seat Positioning with Eye Gaze," filed Oct. 7, 2020, is incorporated herein by reference, in its entirety.

From the foregoing it will be appreciated that, although specific embodiments have been described herein for purposes of illustration, various modifications may be made without deviating from the spirit and scope of the invention. For example, the methods and systems for performing eye gaze control of seat and bed positioning discussed herein are applicable to other architectures. Also, the methods and systems discussed herein are applicable to differing protocols, communication media (optical, wireless, cable, etc.) and devices (such as wireless handsets, electronic organizers, personal digital assistants, portable email machines, game machines, pagers, navigation devices such as GPS receivers, etc.).

The invention claimed is:
1. A microcontroller implemented method in a powered device having a power controlled seat or bed adjustable via actuators, comprising:

presenting a first user interface for selection of a posture axis using eye gaze input, the user interface displaying a plurality of selectable virtual user interface controls each corresponding to an adjustable axis;

receiving, by means of an eye gaze camera and logic configured to detect an occupant's gaze for a determined period of time on a portion of the presented first interface that corresponds to a selected one of the plurality of virtual user interface controls, a selection of an adjustable axis;

presenting a second user interface distinct from the first user interface for selection of an adjustment amount using eye gaze input, the selected adjustment amount to be applied to the selected adjustable axis to cause an adjustment to the power controlled seat or bed;

receiving, by means of the eye gaze camera and logic configured to detect the occupant's second gaze for a determined period of time on a portion of the second presented user interface that corresponds to an adjustment amount, a selection of an adjustment amount;

forwarding the selected adjustable axis and the selected adjustment amount to determine a recommended change and/or overriding values regarding posture of occupant to avoid inadvertent dangers or health issues;

receiving the recommended change and/or overriding values;

determining and modifying the selected adjustable axis and the selected adjustment amount based upon the received recommended change and/or overriding values; and responsive solely to eye gaze input received from the occupant via the first and the second user interfaces and without the occupant typing commands or using oral input, automatically causing actuators to change the modified selected adjustable axis by the modified selected adjustment amount, thereby causing a change to posture of the occupant without the occupant typing commands or using oral input.

2. The method of claim 1 wherein the first and second user interfaces are presented together.

3. The method of claim 1 wherein the adjustment amount specifies a tilt angle.

4. The method of claim 1 wherein the adjustment amount specifies a vertical amount of lift, a recline angle, or a tilt angle.

5. The method of claim 1 wherein the adjustable axis is an axis that controls one or more of leg lift, upper torso recline, seat tilt, seat height, head tilt, or head pan.

6. The method of claim 1, the receiving the recommended change and/or overriding values further comprising:

receiving from a posture and pressure advisor logic an indication that the selected adjustment amount may cause injury or discomfort to the occupant; and causing the selected adjustment amount to be modified to avoid the indicated potential injury or discomfort.

7. The method of claim 6 wherein the causing selected adjustment amount to be modified to avoid the indicated potential injury or discomfort is performed automatically by the microcontroller implemented method without further input from the occupant.

8. The method of claim 6 wherein the indication that the selected adjustment amount may cause injury or discomfort to the occupant is presented on a third user interface as a recommendation that can be accepted or overridden by the occupant, wherein the third user interface may be the same as the first or second user interface.

9. The method of claim 1 wherein the powered device is a wheelchair and the method is performed by code logic executing as part of a display and/or an eye gaze camera.

10. The method of claim 1 wherein the powered device is a hospital bed and the method is performed by code logic executing as part of the display and/or eye gaze camera.

11. An electrically powered device comprising:

an adjustable seat or bed frame capable of adjustments to a plurality of positions affecting posture of an occupant;

one or more actuators configured to adjust the seat or bedframe according to a plurality of axes;

a display with an associated detection device and associated with detection logic to capture eye position, brain waves, or muscle activation of the occupant in order to determine occupant intent to select one or more selectable virtual user interface controls presented on the display; and code logic, configured when executed by a microcontroller, to:

responsive to notification of a selected one of the one or more virtual user interface controls, determining an axis of the seat or bed frame to adjust;

responsive to notification of an adjustment amount, determining an amount to adjust the determined axis;

forward the determined adjustable axis and the determined adjustment amount to determine a recommended change and/or overriding values regarding posture of occupant to avoid inadvertent dangers or health issues;

receive the recommended change and/or overriding values;

modifying the determined adjustable axis and the determined adjustment amount based upon the received recommended change and/or overriding values; and automatically causing one or more actuators associated with the modified axis to change position according to the modified adjustment amount, thereby causing posture of the occupant to change solely responsive to selection of virtual user interface controls using eye gaze input, brain waves, or muscle activation of the occupant without the occupant typing commands or using oral command input.

12. The device of claim 11 wherein the device is a powered wheelchair or a powered hospital bed.

13. The device of claim 11 wherein the display is a room wall or ceiling.

14. The device of claim 11 wherein the detection device is an eye gaze camera.

15. The device of claim 11 wherein the selection of virtual user interface controls is performed using eye gaze input, a brain-computer interface (BCI), and/or an electromyography (EMG) interface.

16. The device of claim 11, further comprising:

logging and telemetry logic configured to report one or more of system diagnostics, usage, positioning activations, and pressure monitoring data to a data repository.

17. The device of claim 11, further comprising:

one or more pressure monitors; and wherein the code logic is further configured, when executed, to:

receive pressure data from the one or more pressure monitors; and determine whether the selected adjustment amount is likely to cause injury or discomfort to the occupant based upon the pressure data.

18. The device of claim 17 wherein the code logic configured to receive pressure data and determine likelihood of injury or discomfort is executed asynchronously and on a continuous basis to monitor occupant input.

19. The device of claim 17 wherein the code logic is configured to cause the selected adjustment amount to be modified to avoid the indicated potential injury or discomfort.

20. The device of claim 19 wherein the code logic is configured to automatically cause the selected adjustment amount to be modified thereby overriding input of the occupant.

21. The device of claim 11 wherein the display associated with the associated detection device is a head mounted system.

22. The device of claim 11, further comprising:
   one or more posture controllers; and
   wherein the code logic is further configured, when executed, to send commands to the one or more posture controllers in order for the one or more posture controllers to automatically cause the one or more actuators associated with the modified axis to change position according to the modified adjustment amount.

23. The device of claim 11 wherein the adjustable axis is an axis that controls one or more of leg lift, upper torso recline, seat tilt, seat height, head tilt, or head pan.

24. A microprocessor implemented method in a powered device having a power controlled seat or bed adjustable via actuators, comprising:
   presenting a first user interface for selection of a posture axis, the user interface displaying a plurality of selectable virtual user interface controls each corresponding to an adjustable axis;
   receiving, by means of a detection device and logic configured to detect an intent of an occupant to select one of the plurality of virtual user interface controls, a selection of an adjustable axis, wherein the detection device is at least one of an eye gaze camera, brain-computer interface, or electromyography interface;
   presenting a second user interface for selection of an adjustment amount to apply to the selected adjustable axis to cause an adjustment to the power controlled seat or bed;
   receiving, by means of the detection device and logic configured to detect an intent of the occupant to select one of the plurality of virtual user interface controls, a selection of an adjustment amount;
   forwarding the selected adjustable axis and the selected adjustment amount to determine a recommended change and/or overriding values regarding posture of occupant to avoid inadvertent dangers or health issues;
   receiving the recommended change and/or overriding values;
   determining and adjusting the selected adjustable axis and the selected adjustment amount based upon the received recommended change and/or overriding values; and
   automatically causing actuators to change the adjusted selected adjustable axis by the adjusted selected adjustment amount responsive solely to selection of virtual user interface controls by eye gaze, brain waves, or muscle activation of the occupant without the occupant typing commands or using oral command input, thereby causing a change to posture of the user.

* * * * *